(12) United States Patent
Jacene et al.

(10) Patent No.: US 9,757,163 B2
(45) Date of Patent: *Sep. 12, 2017

(54) SPINAL PLATE AND DRILL GUIDE

(71) Applicant: DePuy Synthes Products, Inc., Raynham, MA (US)

(72) Inventors: Michael Jacene, Blackstone, MA (US); Michael Gorhan, Mansfield, MA (US); Bacem Georges, Franklin, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 134 days.

This patent is subject to a terminal disclaimer.

(21) Appl. No.: 14/805,252

(22) Filed: Jul. 21, 2015

(65) Prior Publication Data

US 2015/0320455 A1 Nov. 12, 2015

Related U.S. Application Data

(63) Continuation of application No. 11/371,741, filed on Mar. 9, 2006, now Pat. No. 9,119,677.

(60) Provisional application No. 60/749,642, filed on Dec. 9, 2005.

(51) Int. Cl.
| | |
|---|---|
| A61B 17/70 | (2006.01) |
| A61B 17/17 | (2006.01) |
| A61B 17/80 | (2006.01) |

(52) U.S. Cl.
CPC ...... *A61B 17/7059* (2013.01); *A61B 17/1728* (2013.01); *A61B 17/1757* (2013.01); *A61B 17/8038* (2013.01); *A61B 17/8042* (2013.01); *A61B 17/8047* (2013.01)

(58) Field of Classification Search
CPC ................ A61B 17/7059; A61B 17/8042
See application file for complete search history.

(56) References Cited

U.S. PATENT DOCUMENTS

| | | |
|---|---|---|
| 3,488,779 A | 1/1970 | Christensen |
| 3,741,205 A | 6/1973 | Markolf et al. |
| 4,473,068 A | 9/1984 | Oh |

(Continued)

FOREIGN PATENT DOCUMENTS

| | | |
|---|---|---|
| WO | 03/007826 A1 | 1/2003 |
| WO | 03/024344 A1 | 3/2003 |

OTHER PUBLICATIONS

Anderson, P., "The Tether Anterior Cervical Plating System," distributed by Surgical Dynamics.

(Continued)

*Primary Examiner* — Ellen C Hammond
(74) *Attorney, Agent, or Firm* — Nutter McClennen & Fish LLP

(57) ABSTRACT

Bone plates and bone plate systems are provided in which a bone plate includes a plurality of bone screw holes formed therein and positioned in laterally adjacent pairs. Positioned between the laterally adjacent pairs of bone screw holes are stabilizing strut. The bone plate system can additionally include windows positioned between longitudinally adjacent struts. Transverse bone screw planes can extend across the superior and inferior edges of the bone screw holes and define the minimum longitudinal boundaries of the windows. A guide device adapted for mating with the bone plate is also disclosed.

22 Claims, 8 Drawing Sheets

(56) References Cited

U.S. PATENT DOCUMENTS

| | | | |
|---|---|---|---|
| 4,583,541 A | 4/1986 | Barry | |
| 4,686,972 A | 8/1987 | Kurland | |
| 4,696,290 A | 9/1987 | Steffee | |
| 4,905,679 A | 3/1990 | Morgan | |
| 5,030,219 A | 7/1991 | Matsen, III et al. | |
| 5,139,498 A | 8/1992 | Astudillo Ley | |
| 5,180,381 A | 1/1993 | Aust et al. | |
| 5,261,910 A | 11/1993 | Warden et al. | |
| 5,352,224 A | 10/1994 | Westermann | |
| 5,423,826 A | 6/1995 | Coates et al. | |
| 5,487,741 A | 1/1996 | Maruyama et al. | |
| 5,549,612 A * | 8/1996 | Yapp | A61B 17/7059 411/200 |
| 5,569,251 A | 10/1996 | Baker et al. | |
| 5,603,713 A | 2/1997 | Aust et al. | |
| 5,616,144 A | 4/1997 | Yapp et al. | |
| 5,676,666 A | 10/1997 | Oxland et al. | |
| 5,700,266 A | 12/1997 | Harryman, II | |
| 5,746,743 A | 5/1998 | Greenberg | |
| 5,851,207 A | 12/1998 | Cesarone | |
| 5,954,722 A | 9/1999 | Bono | |
| 6,017,345 A | 1/2000 | Richelsoph | |
| 6,030,389 A | 2/2000 | Wagner et al. | |
| 6,071,291 A | 6/2000 | Forst et al. | |
| 6,093,188 A | 7/2000 | Murray | |
| 6,129,730 A | 10/2000 | Bono et al. | |
| 6,139,550 A | 10/2000 | Michelson | |
| 6,152,927 A | 11/2000 | Farris et al. | |
| 6,159,213 A | 12/2000 | Rogozinski | |
| 6,200,322 B1 | 3/2001 | Branch et al. | |
| 6,228,085 B1 | 5/2001 | Theken et al. | |
| 6,331,179 B1 | 12/2001 | Freid et al. | |
| 6,342,057 B1 | 1/2002 | Brace et al. | |
| 6,361,537 B1 | 3/2002 | Anderson | |
| 6,379,364 B1 | 4/2002 | Brace et al. | |
| 6,416,528 B1 | 7/2002 | Michelson | |
| 6,565,571 B1 | 5/2003 | Jackowski et al. | |
| 6,602,255 B1 | 8/2003 | Campbell et al. | |
| 6,679,883 B2 | 1/2004 | Hawkes et al. | |
| 6,689,134 B2 | 2/2004 | Ralph et al. | |
| 6,730,127 B2 | 5/2004 | Michelson | |
| 6,960,211 B1 | 11/2005 | Pfefferle et al. | |
| 7,306,605 B2 | 12/2007 | Ross | |
| 7,527,640 B2 | 5/2009 | Ziolo et al. | |
| 9,119,677 B2 * | 9/2015 | Jacene | A61B 17/1728 |
| 2001/0037112 A1 | 11/2001 | Brace et al. | |
| 2002/0004660 A1 | 1/2002 | Henniges et al. | |
| 2002/0016595 A1 | 2/2002 | Michelson | |
| 2002/0077630 A1 | 6/2002 | Lin | |
| 2002/0082606 A1 | 6/2002 | Suddaby | |
| 2002/0151899 A1 | 10/2002 | Bailey et al. | |
| 2003/0083658 A1 | 5/2003 | Hawkes et al. | |
| 2003/0105462 A1 | 6/2003 | Haider | |
| 2003/0208204 A1 | 11/2003 | Bailey et al. | |
| 2003/0233098 A1 | 12/2003 | Markworth | |
| 2004/0015174 A1 | 1/2004 | Null et al. | |
| 2004/0039387 A1 | 2/2004 | Gause et al. | |
| 2004/0068319 A1 | 4/2004 | Cordaro | |
| 2004/0092947 A1 | 5/2004 | Foley | |
| 2004/0097925 A1 | 5/2004 | Boehm et al. | |
| 2004/0204712 A1 | 10/2004 | Kolb et al. | |
| 2004/0204717 A1 | 10/2004 | Fanger et al. | |
| 2004/0220571 A1 | 11/2004 | Assaker et al. | |
| 2004/0239387 A1 | 12/2004 | Zhang et al. | |
| 2005/0027297 A1 | 2/2005 | Michelson | |
| 2005/0027298 A1 | 2/2005 | Michelson | |
| 2005/0033294 A1 | 2/2005 | Garden et al. | |
| 2005/0049593 A1 | 3/2005 | Duong et al. | |
| 2005/0065521 A1 | 3/2005 | Steger et al. | |
| 2005/0137597 A1 | 6/2005 | Butler et al. | |
| 2005/0149032 A1 | 7/2005 | Vaughen et al. | |
| 2005/0182408 A1 | 8/2005 | Pfefferle et al. | |
| 2005/0192577 A1 | 9/2005 | Mosca et al. | |
| 2005/0228386 A1 | 10/2005 | Ziolo et al. | |
| 2005/0283152 A1 | 12/2005 | Lindemann et al. | |
| 2005/0288790 A1 | 12/2005 | Swords | |
| 2006/0025772 A1 | 2/2006 | Leibel et al. | |
| 2006/0058796 A1 | 3/2006 | Hartdegen et al. | |
| 2006/0122604 A1 | 6/2006 | Gorhan et al. | |
| 2006/0149251 A1 | 7/2006 | Ziolo et al. | |
| 2006/0161157 A1 | 7/2006 | Mosca et al. | |
| 2006/0217723 A1 | 9/2006 | Suh | |
| 2007/0123879 A1 | 5/2007 | Songer et al. | |
| 2007/0123884 A1 | 5/2007 | Abdou | |
| 2007/0162013 A1 | 7/2007 | Jacene et al. | |
| 2008/0234680 A1 | 9/2008 | Zaiser et al. | |
| 2009/0192549 A1 | 7/2009 | Sanders et al. | |
| 2009/0216282 A1 | 8/2009 | Blake et al. | |

OTHER PUBLICATIONS

AXIS Fixation System product brochure, Sofamor Danek, Memphis, TN, 1997.

Blackstone Anterior Cervical Plate, Blackstone Medical, Inc., product brochure.

DePuy ACE product line, DePuy Orthopaedics, Inc., 2004.

DOC Ventral Cervical Plate System, DePuy AcroMed Inc., product catalog, 2001.

Richter, M. et al., "Biomechanical Evaluation of a Newly Developed Monocortical Expansion Screw in the Anterior Internal Fixation of the Cervical Spine—In-Vitro Comparison with 2 Established Internal Fixation Systems," Department of Orthopedics, Univ. of Ulm, Germany, Feb. 1, 1999.

SC-AcuFix, Spinal Concepts, Inc., Feb. 2000.

SUMMIT Fixation System, DePuy AcroMed Inc., product catalog, 2000.

* cited by examiner

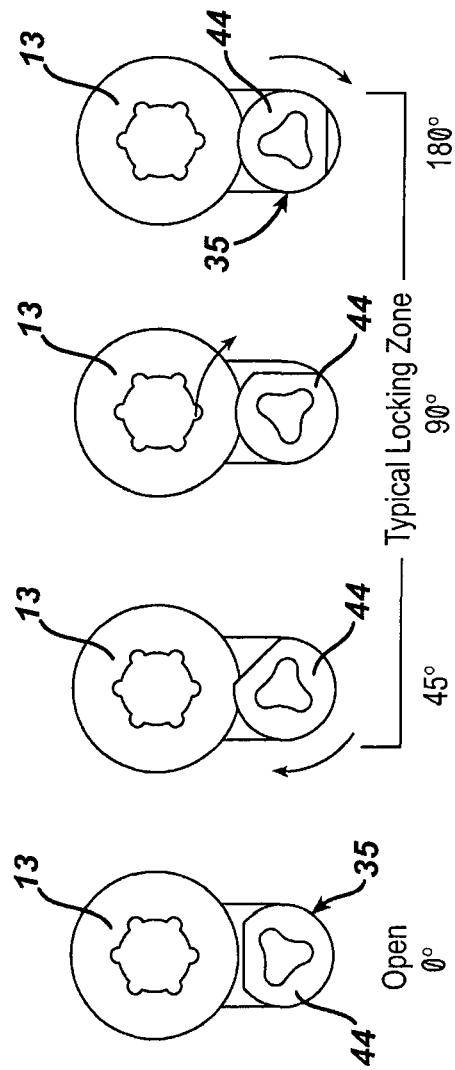

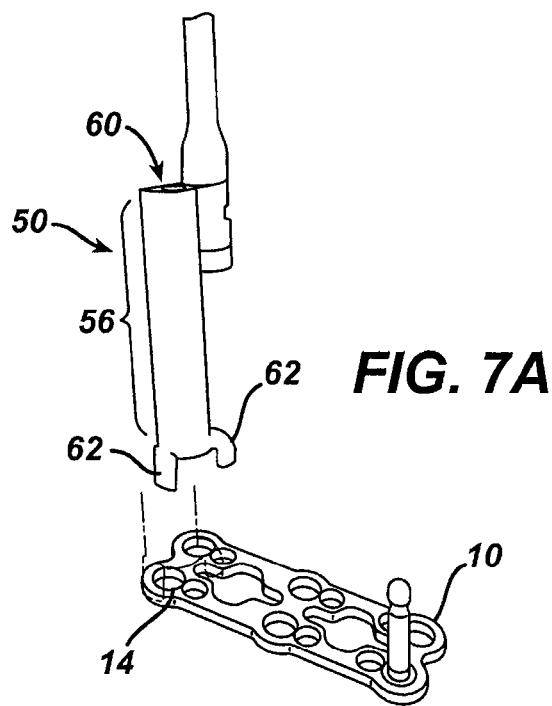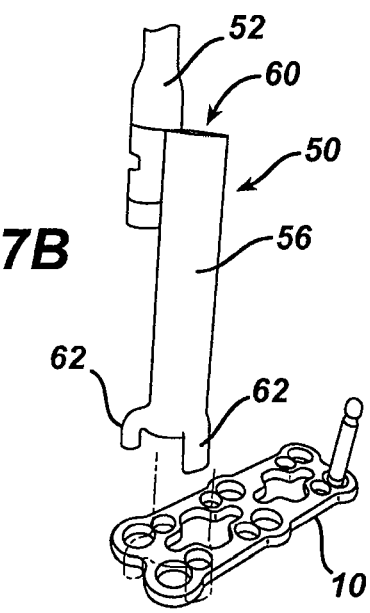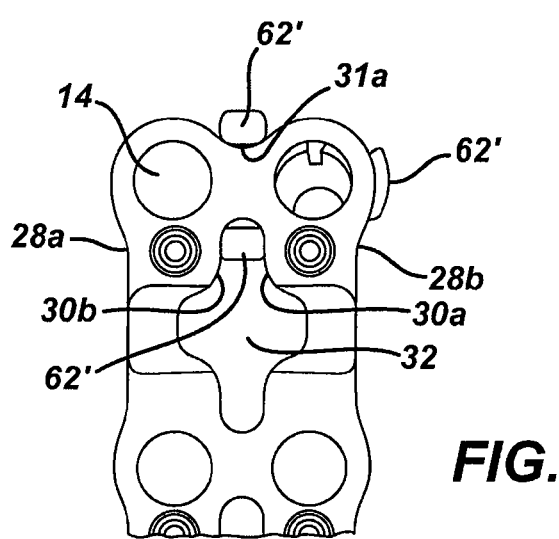
FIG. 7A
FIG. 7B
FIG. 7C

SPINAL PLATE AND DRILL GUIDE

CROSS REFERENCE TO RELATED APPLICATION

This Application is a continuation of U.S. application Ser. No. 11/371,741 filed Mar. 9, 2006 and entitled "Spinal Plate and Drill Guide," which claims the benefit of priority to U.S. Provisional Application Ser. No. 60/749,642 filed Dec. 9, 2005 and entitled "Spinal Plate and Drill Guide," which are each hereby incorporated herein by reference in their entirety.

BACKGROUND

For a number of known reasons, bone fixation devices are useful for promoting proper healing of injured or damaged vertebral bone segments caused by trauma, tumor growth, or degenerative disc disease. The fixation devices immobilize the injured bone segments to ensure the proper growth of new osseous tissue between the damaged segments. These types of bone fixation devices often include internal bracing and instrumentation to stabilize the spinal column to facilitate the efficient healing of the damaged area without deformity or instability, while minimizing any immobilization and post-operative care of the patient.

One such device is an osteosynthesis plate, more commonly referred to as a bone fixation plate, that can be used to immobilize adjacent skeletal parts such as bones. Typically, the fixation plate is a rigid metal or polymeric plate positioned to span bones or bone segments that require immobilization with respect to one another. The plate is fastened to the respective bones, usually with bone screws, so that the plate remains in contact with the bones and fixes them in a desired position. Bone plates can be useful in providing the mechanical support necessary to keep vertebral bodies in proper position and bridge a weakened or diseased area such as when a disc, vertebral body or fragment has been removed.

Such plates have been used to immobilize a variety of bones, including vertebral bodies of the spine. These bone plate systems usually include a bone plate having a plurality of screw openings. The openings are either holes or slots to allow for freedom of screw movement. The bone plate is placed against the damaged vertebral bodies and bone screws are used to secure the bone plate to the spine, usually with the bone screws being driven into the vertebral bodies. Exemplary systems are described in U.S. Pat. No. 6,159,213 to Rogozinski; U.S. Pat. No. 6,017,345 to Richelsoph; U.S. Pat. No. 5,676,666 to Oxland et al.; U.S. Pat. No. 5,616,144 to Yapp et al.; U.S. Pat. No. 5,549,612 to Yapp et al.; U.S. Pat. No. 5,261,910 to Warden et al.; and U.S. Pat. No. 4,696,290 to Steffee.

Despite the existence of these bone plate systems, there remains a need for a bone plate system that can provide increased visualization of a surgical site to facilitate alignment and implantation of bone plate, while providing sufficient strength and rigidity to immobilize the bone to which it is implanted.

SUMMARY

Disclosed herein are bone plate systems including a bone plate having a unique geometry that renders the plate effective and convenient to install. In spinal plate applications, for example, the plate provides for enhanced visibility of the interface between the disc or implant and vertebral bodies and can also provide enhanced visibility of the vertebral bodies.

In one embodiment, an implantable bone plate is provided. The bone plate has a longitudinal axis extending from a superior end to an inferior end and a plurality of bone screw holes. The bone screw holes can be aligned in the plate in laterally adjacent pairs, wherein each laterally adjacent pair of bone screw holes has a stabilizing strut extending between each laterally adjacent bone screw hole of the pair. In addition, each of the laterally adjacent pairs of bone screw holes can define a transverse plane (i.e., a "transverse bone screw hole plane") extending between an edge of each laterally adjacent bone screw hole of the pair. The plate further includes a window formed in the plate and extending longitudinally between the laterally adjacent pairs of bone screw holes. At one end, the window can have a superior boundary that extends at least to the transverse bone screw hole plane of a first laterally adjacent pair of bone screw holes. In one aspect, the window also includes an inferior boundary that extends at least to the transverse bone screw hole plane of a second laterally adjacent pair of bone screw holes that is spaced longitudinally from the first adjacent pair of bone screw holes.

In one aspect, the bone plate is a two level plate and comprises two windows and three pairs of laterally adjacent bone screw holes. Alternatively, the bone plate could be a single level plate or a three (or more) level plate.

In another aspect, the bone plate window extends longitudinally beyond at least one of the superior boundary and inferior boundary of a transverse bone screw hole plane. The bone plate window can have a variety of shapes and sizes and can, for example, extend longitudinally and transversely.

To facilitate mating of the plate to a surgical tool, the bone plate can include recessed areas at the superior and inferior ends of the plate. For example, the recessed areas can be positioned at the inferior and superior ends of the plate. The bone plate can also include a bone screw locking mechanism. In one aspect, the bone screw locking mechanism comprises a rotatable cam integrated with the plate.

In another embodiment, an implantable bone plate system is provided. The system includes an implantable bone plate and a drill guide adapted to mate with the bone plate. The bone plate can include a plate body having a longitudinal axis and a plurality of bone screw holes. The bone screw holes can be aligned in the plate in laterally adjacent pairs, wherein each laterally adjacent pair of bone screw holes has a stabilizing strut extending between each laterally adjacent bone screw hole of the pair. In addition, each of the laterally adjacent pairs of bone screw holes can define a transverse bone screw plane extending between an edge of each laterally adjacent bone screw hole of the pair. The plate can further include at least one window having a superior boundary that extends at least to the transverse bone screw hole plane of a first laterally adjacent pair of bone screw holes and an inferior boundary that extends at least to the transverse bone screw hole plane of a second laterally adjacent pair of bone screw holes that is spaced longitudinally from the first adjacent pair of bone screw holes.

The system also includes a guide device adapted for use with the bone plate. In one aspect, the guide device comprises a guide barrel and at least one feature extending from a distal end of the guide barrel. The guide device can be adapted to register with a sidewall of the window and an outer sidewall of the plate body.

In one aspect, the at least one feature of the guide device include first, second, and third features. The first feature can be adapted to mate with a recessed portion of the plate body sidewall, the second feature can be adapted to mate with another portion of the plate body outer sidewall, and the third feature can be adapted to mate with an inner side wall of the window.

In another aspect, the at least one feature of the guide device includes multiple tabs. The tabs can be spaced to receive a portion of the bone plate therebetween. For example, at least one of the tabs can be adapted to be positioned against the sidewall of the window and at least one of the tabs is adapted to be positioned against the outer sidewall of the bone plate.

BRIEF DESCRIPTION OF THE DRAWINGS

The invention can be more fully understood from the following detailed description taken in conjunction with the accompanying drawings, in which:

FIG. 6A is a sectional, top view of a bone screw and a bone screw locking mechanism;

FIG. 6B is a top view of the locking mechanism of FIG. 6A rotated 45°;

FIG. 6C is a top view of the locking mechanism of FIG. 6A rotated 90°;

FIG. 6D is a top view of the locking mechanism of FIG. 6A rotated 180°;

FIG. 7A is a perspective view of one embodiment of a bone plate system described herein;

FIG. 7B is another perspective view of the bone plate system of FIG. 7A;

FIG. 7C is a bottom view of the bone plate system of FIG. 7A;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The following exemplary embodiments are described herein with reference to bone plates used to span and immobilize adjacent vertebral bodies in spinal fixation techniques. However, it is understood that the bone plate systems described herein may be applicable to the fixation of any type of adjacent bones or bone segments. In addition, one skilled in the art will appreciate that while plate 10 is described as being fixed to bone, the term "bone" is used broadly and includes applications in which a layer of soft tissue is covering all or a portion of the hard tissue surface.

In one embodiment, disclosed herein is a bone plate including a plate body that extends along a longitudinal axis and has a plurality of apertures defining bone screw holes for receiving bone screws. The plate body can also include stabilizing struts and a viewing window. For example, in one aspect, at least some of the bone screw holes are positioned in laterally adjacent pairs, the laterally adjacent pairs of bone screw holes being spaced longitudinally from each other. Extending between the laterally adjacent pairs of bone screws are struts that provide rigidity to the plate. Openings in the plate, positioned between the struts, can provide a viewing window that enhances visibility of an implant, disc, and/or vertebral body (midline and/or endplate).

The plate illustrated and described in the exemplary embodiments is particularly well suited for placement on the spine. The plate can be in the form of a single level plate, which spans two adjacent vertebral bodies, or a multilevel plate that spans three or more adjacent vertebral bodies.

Figure 1:
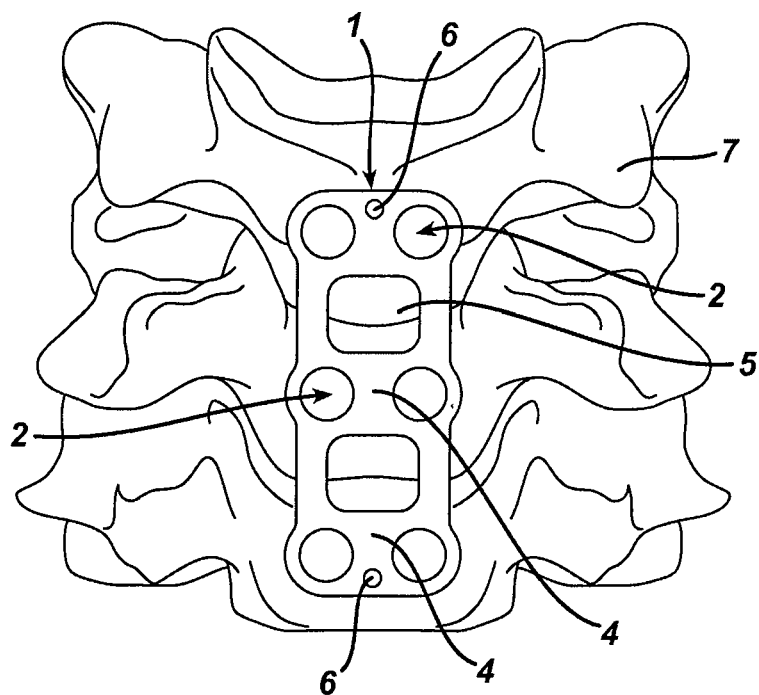
FIG. 1 is a prior art fixation device mounted on a spinal column.
Figure 2:
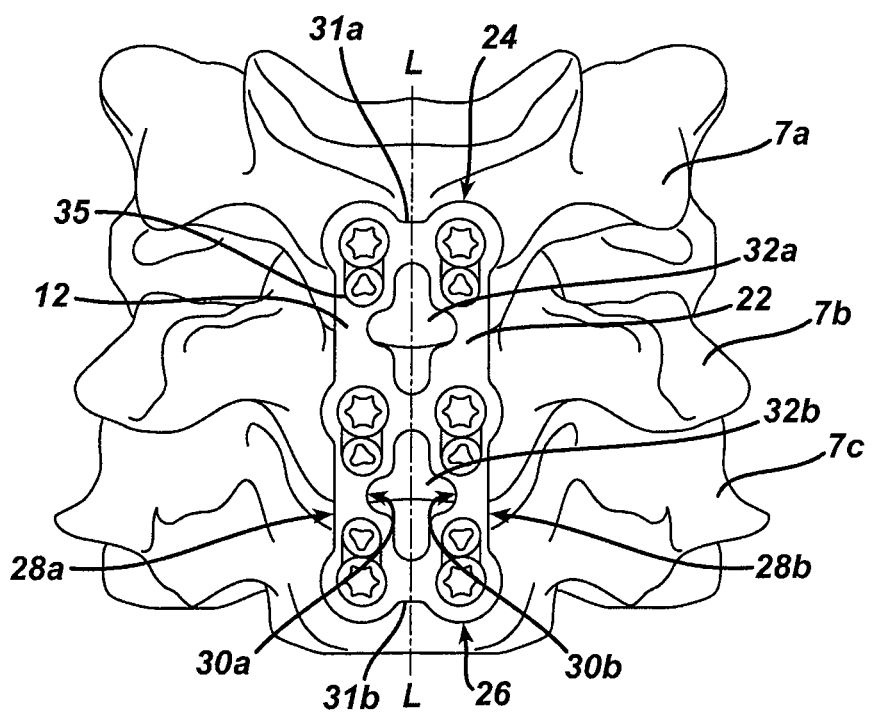
FIG. 2 is a front view of one embodiment of an implantable bone plate, as described herein, positioned on a spinal column.

FIG. 1 illustrates a previously known bone plate 1 having a plurality of bone screw holes 2 and fixation pin-receiving holes 6. Conventional bone plates, such as bone plate 1, provide somewhat limited visibility of the vertebrae due to substantially closed regions 4 that extend around laterally opposed bone screw holes 2. As a result, visualization windows 5, disposed between closed regions 4, provide limited visibility of vertebral bodies 7 and the disc/vertebral body interface. While windows 5 allow some visibility of the intervertebral space, the expansive nature closed regions 4 can make plate positioning and implant inspection more difficult. In contrast, disclosed herein is plate 10 which, as illustrated in FIG. 2 mounted upon an anterior cervical surface of a spine, has open areas 32a, 32b that have dimensions and a configuration that provides enhanced visualization of the vertebral bodies 7a, 7b, 7c on which the plate is to be mounted and of the disc/vertebral body interface. In addition, plate 10 includes transverse struts that provide sufficient plate rigidity, while having a small profile that maximizes visibility.

Figure 3:
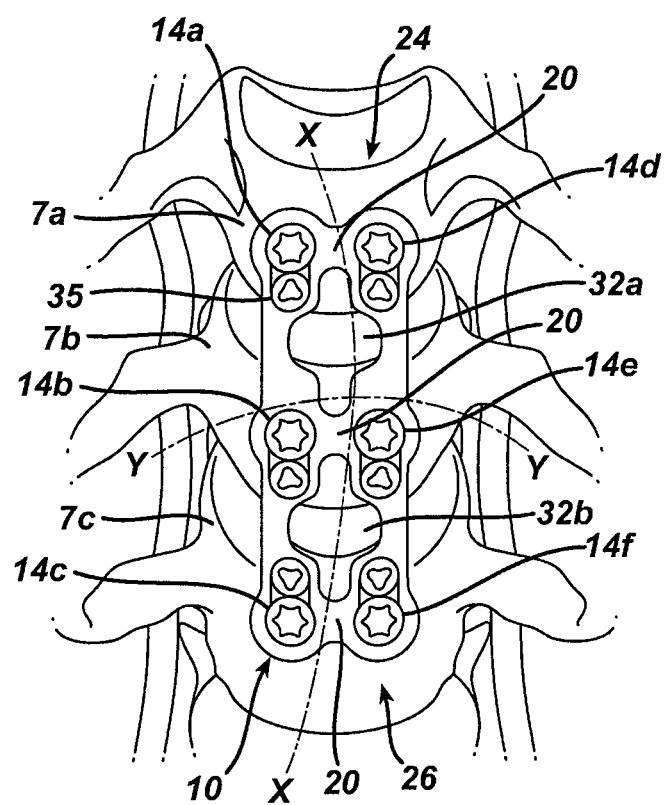
FIG. 3 illustrates another embodiment of the implantable bone plate described herein.
Figure 4:
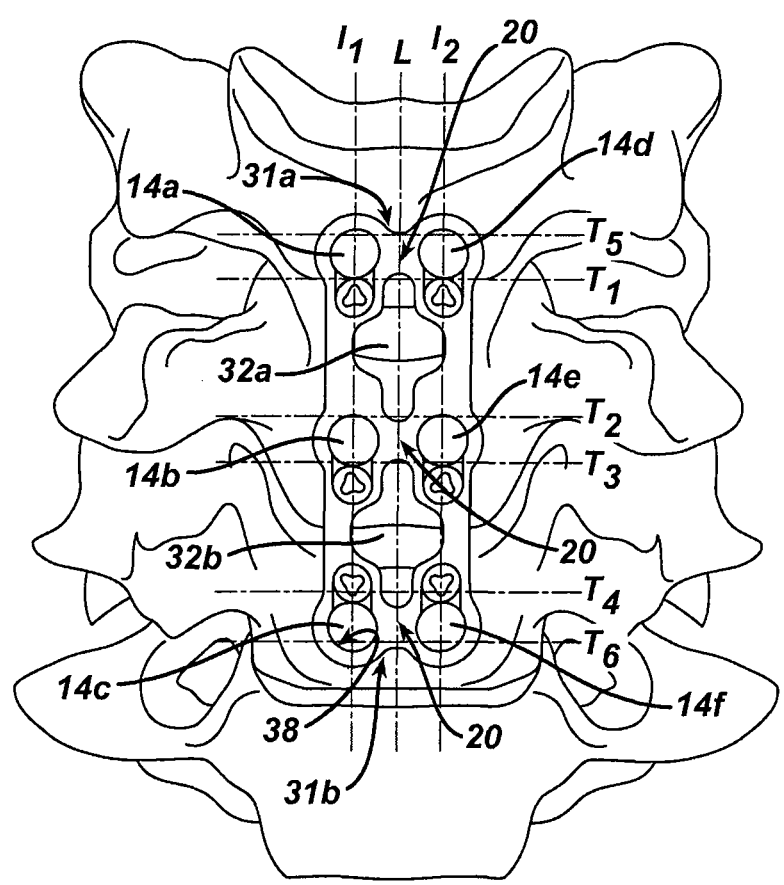
FIG. 4 illustrates yet another embodiment of the implantable bone plate described herein.

FIGS. 2 through 4 illustrate one exemplary embodiment of bone plate 10 as disclosed herein. With respect to FIG. 2, bone plate 10 includes a plate body 12 that extends longitudinally along axis L from a superior end 24 to an inferior end 26 and that is sized and shaped for positioning on vertebral bodies. The plate body has a bone contacting surface (not shown) and an opposed, non-bone contacting surface 22. Further, body 12 has outer sidewalls 28a, 28b, which define the outer edge of the plate, and inner sidewalls 30a, 30b (defining open area 32b discussed below), which are opposed to one another. Positioned on plate body 12 are a plurality of bone screw holes 14a, 14b, 14c, 14d, 14e, 14f, (FIG. 3) and stabilizing struts 20 (FIG. 3). The open areas 32a, 32b, as noted above, are positioned between struts 20.

Bone plate 10, as illustrated in FIGS. 2 through 4, includes a width that varies along the longitudinal axis of the plate. The outer sidewalls 28a, 28b, can be substantially linear, except adjacent to bone screw holes 14a through 14f where they are somewhat curved as discussed below. The shape of outer sidewalls 28a, 28b can provide additional width of the plate as measured across the bone screw holes while minimizing the plate size adjacent to windows 32a, 32b. The shape of the bone plate can also facilitate mating with a guide device as explained below.

In one aspect, the outer and inner sidewalls of the plate surrounding bone screw holes 14 have a curved shape. In particular, the outer and inner sidewalls adjacent bone screw holes 14 at superior 24 and inferior 26 ends of the plate can follow a curvature that matches at least a portion of the curvature of an inner wall 38 (FIG. 4) that defines the bone screw holes 14. The outer sidewall of the bone plate adjacent the bone screw holes at the superior 24 and inferior 26 ends of the plate thus can follow a curvature that is at least partially circular.

In addition, the superior and inferior ends 24, 26 of plate body 12 can have recessed regions 31a, 31b (FIG. 4). In one embodiment, in addition to minimizing the profile of plate body 12, recessed regions 31a, 31b facilitate mating of plate 10 with a surgical tool as discussed below.

Outer sidewall 28a, 28b adjacent the bone screw holes 14b, 14e in the middle portion of the plate can also be curved. For example, the plate sidewall adjacent to bone screw holes 14b, 14e can curve outward to accommodate the diameter of bone screw holes 14b, 14e. In one aspect, the curved portions of plate body 12 adjacent to bone screw holes 14a, 14e are complementary to a corresponding segment of inner wall 38 of the bone screw holes.

Bone plate 10 disclosed herein can have features that facilitate mounting of bone plate 10 on a vertebral column, such as, for example, a preformed curvature that is complementary to the vertebrae upon which the plate is to be mounted. For example, the bone-contacting surface of the exemplary plate 10 can have a longitudinal curve X (FIG. 3) that approximates the lordotic curvature of the vertebrae upon which the plate is to be mounted. For example, the plate can have a longitudinal curve X that extends in the sagital plane (i.e., in the superior-inferior direction) and that has constant radius along the length of the plate 10. Alternatively, the plate 10 may comprise a plurality of longitudinal segments that are configured to collectively provide the plate with a longitudinal curvature that approximates the lordotic curvature of the vertebrae. For example, one or more of the longitudinal segments may have a longitudinal curvature or may be oriented at angle relative to the other longitudinal segments.

While the exemplary plate 10 may be curved only along longitudinal axis L, in another embodiment, plate 10 can also include a transverse curve Y (FIG. 3) that approximates the transverse curvature of the vertebrae upon which the plate is to be mounted. The plate 10 may have a transverse curvature along the length of the plate 10 or along discrete longitudinal segments of the plate. For example, the middle portion of the exemplary plate 10 may have a transverse curvature that approximates the transverse curvature of the vertebrae. Alternatively, the superior end 24 and/or the inferior end 26 may have a different transverse curvature.

The bone plate, as mention above, further includes a plurality of bone screw holes 14 formed along the bone plate and extending through the plate from the non-bone contacting surface 22 to the bone contacting surface. In addition, plate body 12 can include locking mechanisms 35 (FIG. 2) adapted to lock bone screws in bone screw holes.

In one aspect, the bone screw holes are positioned in laterally adjacent pairs. For example, a first bone screw hole in each pair can be positioned along longitudinal axes $l_1$, and a second bone screw hole in each pair can be positioned along longitudinal axis $l_2$. In addition, as shown in FIG. 4, the bone screw hole pairs are spaced longitudinally such that longitudinally adjacent bone screw holes (e.g., holes 14a, 14b and 14b, 14c) will be positioned on different vertebral bodies when the bone plate is implanted within a patient. In the embodiments illustrated in FIGS. 2 through 4, bone plate 10 is a two level plate having three bone screw hole pairs, each pair of bone screw holes corresponding to a different vertebral body 7a, 7b, 7c. Other types of plates are also contemplated, including, for example, a single level plate having two pairs of opposed bone screw holes. In addition, other plates, such as three or more level plates are also contemplated.

Plate body 12 can further include at least one strut 20 that extends transversely between laterally adjacent bone screw holes. In one aspect, struts are positioned between each pair of laterally adjacent bone screws to provide support to plate 10. When bone plate 10 is implanted, the area of plate body 12 adjacent to bone screw holes 14 is subject to stress. Struts 20 can support plate 10 in these high stress areas and provide plate rigidity.

However, unlike conventional bone plates which have a large closed region around bone screw holes, struts 20 have a minimum profile and thus are adapted to provide maximum visibility. In particular, plate 10 can include an open space that extends between struts 20, and in one embodiment open spaces 32a, 32b extend longitudinally between each adjacent strut 20. The open spaces 32a, 32b, as noted above, provide enhanced visibility of the vertebral bodies onto which plate 10 is to be mounted. In particular, the open spaces 32a, 32b can be useful to ensure proper alignment of the plate on the vertebral bodies. For example, the open spaces can allow a partial midline view of the vertebrae to facilitate a midline alignment of plate 10 on the vertebral bodies. In addition, the open spaces can allow inspection of the intersection of vertebral body 7 and an implant or disc.

In one aspect, at least one end of the open spaces can extend at least to a transverse bone-screw-hole plane defined by the edges of laterally adjacent bone screw pairs. As shown in FIG. 4, the inferior edges of bone screw holes 14a, 14d define a transverse plane $T_1$ and the superior ends of bone screw holes 14b, 14e define a transverse plane $T_2$. Window 32a can extend at least from transverse plane $T_1$ to at least transverse plane $T_2$. Similarly, window 32b can extend between a transverse plane $T_3$ and a transverse plane $T_4$ defined by the inferior edges of bone screw holes 14b, 14e and by the superior edges of bone screw holes 14c, 14f, respectively.

The recessed areas 31a, 31b at the superior and inferior ends 24, 26 of plate body 12 can similarly extend to a transverse plane defined by the edges of bone screw holes 14a, 14c, 14d, 14f. For example, the superior ends of bone screw holes 14a, 14d can define a transverse plane $T_5$ and the inferior ends of bone screw holes 14c, 14f can define a transverse plane $T_6$. Recessed area 31a, can extend toward the inferior end of plate body 12 to transverse plane $T_5$, and recessed area 31b can extend toward the superior end of plate body 12 to transverse plane $T_6$.

In another embodiment, window 32a, window 32b, and/or recessed areas 31a, 31b can extend beyond transverse planes $T_1$, $T_2$, $T_3$, $T_4$, $T_5$, $T_6$. For example, in FIG. 4, the inferior end of window 32a extends beyond transverse plate T₂, while the superior end of window 32a does not. The choice of how far to extend windows 32a, 32b can depend, for example, on the placement of an implant and/or the need to view a particular portion of the anatomy.

Windows 32a, 32b can have a variety of shapes and sizes. In one embodiment, windows 32a, 32b extend transversely as shown in FIG. 2. For example, the mid portion of windows 32a, 32b can extend transversely toward the sidewalls 28a, 28b of plate body 12 and define windows having generally "plus" shapes. The "plus" shaped windows are one example of a window shape that can provide a maximum viewing area while allowing enough space on plate body 12 for locking mechanisms 35. One skilled in the art will appreciate that windows 32a, 32b can have a variety of other shapes such as oval, round, rectangular, triangular, and irregular. In addition, windows 32a, 32b can each have different shapes.

In addition, while a single strut is illustrated for each pair of laterally adjacent bone screw holes and a single window extends between adjacent struts, plate body 12 can include additional struts (not shown) and additional windows (not shown) at any point along the length of the plate. In one embodiment, plate body 12 can include more than a single window between each adjacent strut. For example, side-by-side windows could be positioned between adjacent struts. Alternatively, plate body 12 could include additional struts (i.e., more struts than pairs of laterally adjacent bone screw holes) and additional windows between the additional struts. In yet another embodiment, plate body 12 could include fewer struts (and windows) than the number of laterally adjacent pairs of bone screw holes.

Figure 5A:
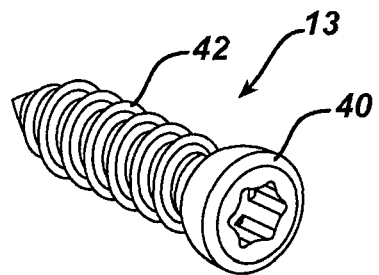
FIG. 5A illustrates a perspective view of one embodiment of a bone screw for use with the bone plate described herein
Figure 5B:
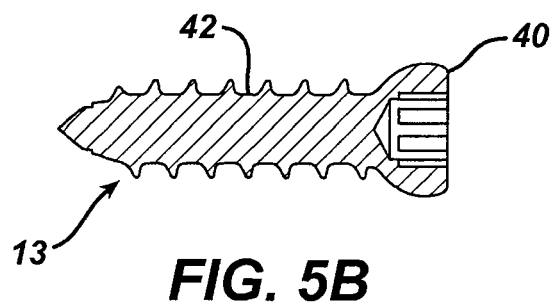
FIG. 5B illustrates a cross sectional view of the bone screw of FIG. 5A.

In another embodiment, a bone plate system, including bone plate 10 and bone screws 13, is disclosed. FIGS. 5A and 5B illustrate an exemplary bone screw 13 that has a proximal head portion 40 and a distal threaded shank 42. Head 40 can be shaped and dimensioned to sit within bone screw hole 14 when implanted into bone to fix bone plate 10 in position. One skilled in the art will that bone screw 13 is exemplary and that a variety of other bone screws or other fixation devices can be used with the bone plate system.

Figure 5C:
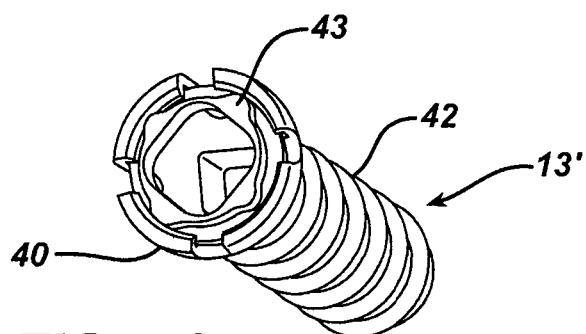
FIG. 5C is a perspective view of yet another bone screw includes a locking mechanism.

Once bone screw 13 is implanted through bone plate 10, a surgeon can lock the bone screws to bone plate 10 to prevent screw backout. For example, the various embodiments of the spinal plates disclosed herein can include a locking or retaining mechanism for locking the bone screw to the bone plate and preventing bone screw backout. In one embodiment, the locking mechanism can be integrated into the screw head, as described in a U.S. patent application Ser. No. 10/904,992, entitled "Locking Bone Screw and Spinal Plate System" of Gorhan et al., which is incorporated by reference herein in its entirety. For example, FIG. 5C illustrates bone screw 13' with an integrated locking cam 43 rotatably positioned within bone screw head 40. In use, bone screw 13' can be seated in bone screw holes 14 and the locking cam 43 can be rotated to provide bone screw backout resistance.

In another embodiment, the locking mechanism can be integrated onto the surface of the plate. The integrated locking mechanism can be, for example, a cam that is rotatable between an unlocked position and a locked position, in which the cam is forced against the head of the bone screw to provide bone screw backout resistance. For example, FIGS. 6A through 6D illustrate cam 44 rotatably positioned adjacent to bone screw 13 in bone screw hole 14 of bone plate 10. Other exemplary cam-type locking mechanisms are described in U.S. Pat. No. 5,549,612 of Yapp et al. entitled "Osteosynthesis Plate System," which is also incorporated by reference herein in its entirety. Other exemplary retaining or locking mechanisms include, by way of non-limiting example, locking washers, locking screws, and bone screw covers. One skilled in the art will appreciate that various combinations of locking mechanisms can be used as well. Other exemplary locking mechanisms are disclosed in U.S. Pat. No. 6,331,179 to Fried et al., U.S. Pat. No. 6,159,213 to Rogozinski; U.S. Pat. No. 6,017,345 to Richelsoph; U.S. Pat. No. 5,676,666 to Oxland et al.; U.S. Pat. No. 5,616,144 to Yapp et al.; U.S. Pat. No. 5,261,910 to Warden et al.; and U.S. Pat. No. 4,696,290 to Steffee.

It is understood that the bone plate system may include different types of bone screws having varying functionalities. For example, the bone screws can be of a rigid type in which after a screw locking mechanism is engaged, movement of the screw in any direction is prevented. The bone screws can also be of a semi-rigid type in which after a screw locking mechanism is engaged, screw backout is prevented, but the screw is able to move in all directions (i.e., polyaxially). Further, the bone screws can also be of a hybrid type in which after a screw locking mechanism is engaged, screw backout is prevented, but the screw is able to move in only one selected direction (e.g., the superior-inferior or the transverse direction). Moreover, the bone screws may translate within an aperture of a plate. For example, a bone screw may translate along the length of an elongated slot defining an aperture in the plate. One skilled in the art will appreciate that a bone plate system may be provided having any single screw type or a combination of all or any of the screw types.

The bone plate system can also include a surgical tool such as, for example, a guide device 50 adapted to mate with bone plate 10 in registration with bone screw holes 14. An exemplary guide device 50 is shown in FIGS. 7A and 7B. Guide device 50 generally includes an elongate shaft 52 having a proximal handle portion (not shown) and a distal end coupled to a guide member 56. The shaft 52 may be offset from, and angled with respect to, guide member 56, as shown in FIGS. 7A and 7B. Guide member 56 includes a least one pathway 60 extending therethrough with one or more alignment members 62 extending from a distal portion thereof. Alignment members 62 can be spaced apart such that they are adapted to engage and/or align with a portion of the bone plate adjacent to and external of bone screw holes 14.

In one embodiment, pathway 60 is sized (i.e., in diameter) and shaped to allow the passage of a variety of bone preparation surgical tools (e.g., drill, tap, etc.) and bone screws 13 through pathway 60 and into bone beneath bone plate 10. In use, alignment members 62 are positioned external to bone screw hole 14 to position pathway 60 in registration with a bone screw hole. Once registration is achieved, the bone beneath bone plate 10 can be prepared (e.g., drilling, tapping, etc.), and bone screws subsequently can be implanted into the prepared bone through pathway 60 without removing guide device 50.

Alignment elements 62 can include four tabs 62' (best seen in FIG. 7C) adapted to engage the outer sidewalls of bone plate 12 adjacent to the bone screw holes and the inner sidewall(s) 30a, 30b of open area 32. The tabs can be shaped to match the curved profile of the sidewalls adjacent to the bone screw holes. For example, a guide device adapted to register with the bone screw holes in the plate illustrated in FIGS. 2 through 4 would have tabs 62' adapted to match recessed area 31a (31b) on one side of one of the struts strut 20, open area 32 on the other side of the strut, and the outer sidewall 28a, 28b of the plate adjacent to the bone screw hole. In one aspect, the relative dimensions of the space between tabs 62' and the width of the plate adjacent bone screw holes can be such that guide device 50 achieves an interference fit with plate body 12. Such an interference fit would enable the guide device 50 to engage the plate in a manner that enables it to function as a plate holder. One skilled in the art will appreciate the shape and spacing of tabs 62' can also be adapted to form a variety of other fits with bone plate 10, such as a sliding clearance fit.

Figure 8A:
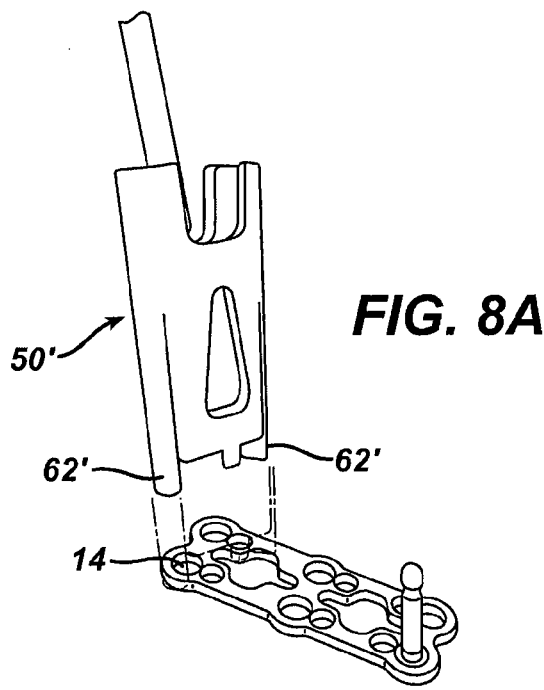
FIG. 8A is a perspective view of another embodiment of a bone plate system described herein.
Figure 8B:
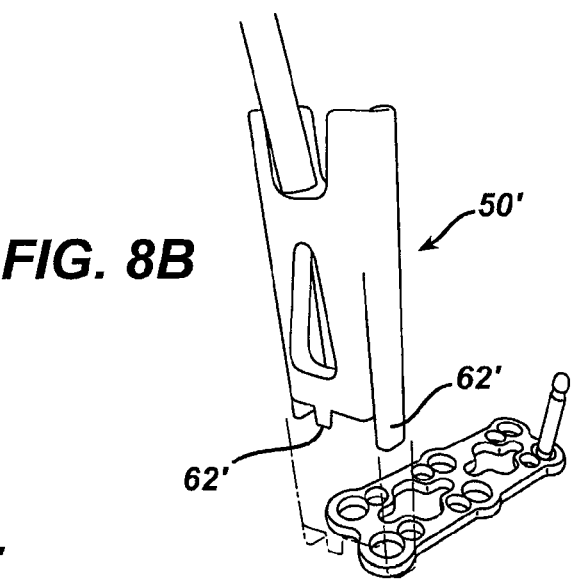
FIG. 8B is another perspective view of the bone plate system of FIG. 8A.
Figure 8C:
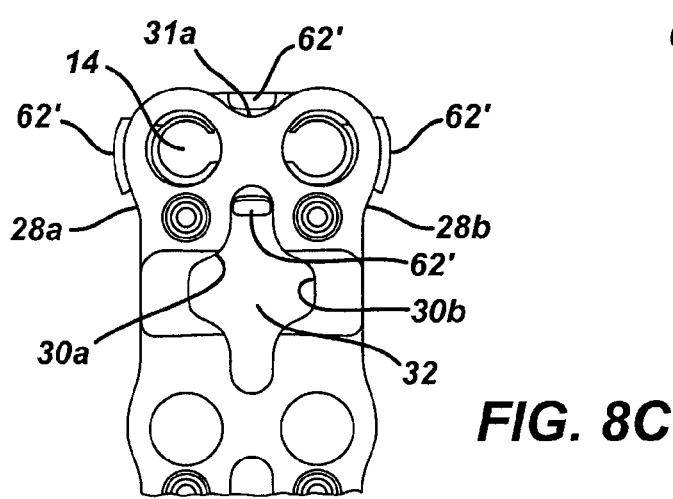
FIG. 8C is a bottom view of the bone plate system of FIG. 8A.

In one embodiment, guide device 50 is a single barrel device adapted to register with a single bone screw hole and having a single pathway 60 through the guide member 56 as shown in FIGS. 7A and 7B. In another embodiment, illustrated in FIGS. 8A, 8B, and 8C a guide device 50' could include multiple pathways for registering with multiple bone screw holes 14 at the same time. For example, the multiple pathways can be spaced such that when the guide device is mated to bone plate 10, the pathways register with two or more bone screw holes 14. One such exemplary guide device is disclosed in application Ser. No. 10/776,414, entitled "Guide For Spinal Tools, Implants, and Devices," filed Feb. 11, 2004 and incorporated hereby reference in its entirety. The alignment elements on the dual pathway guide device can similarly include two tabs that extend from the distal portion of the single guide member. In use, tabs 62' can mate with the outer sidewall 28a, 28b of plate body (and span opposed bone screw holes), recessed areas 31a, 31b, and/or open area 32.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. An implantable bone plate, comprising:
an elongate plate having first and second parallel longitudinal axes;
a plurality of bone screw holes, the bone screw holes being aligned on the first and second longitudinal axes in laterally adjacent pairs;
a plurality of rotatable cams each being disposed adjacent to a respective one of the plurality of bone screw holes, each cam being rotatable between an unlocked position and a locked position; and
a plus-shaped window formed in the plate and extending longitudinally between the laterally adjacent pairs of bone screw holes, the window having:
a superior portion defined by opposed lateral sidewalls and a superior sidewall, the superior portion being at least partially disposed between first and second cams of the plurality of cams,
an inferior portion defined by opposed lateral sidewalls and an inferior sidewall, and
a mid-portion extending between the superior and inferior portions, the mid-portion having a width extending between opposed lateral sidewalls that is greater than a width extending between the opposed lateral sidewalls of the superior and inferior portions.

2. The bone plate of claim 1, wherein each laterally adjacent pair of bone screw holes has a stabilizing strut extending between each laterally adjacent bone screw hole of the pair.

3. The bone plate of claim 1, wherein the superior and inferior portions of the window extend longitudinally and the mid-portion of the window extends transversely.

4. The bone plate of claim 1, further comprising recessed areas adjacent to struts at superior and inferior ends of the plate, the recessed areas being formed in an outer periphery of the plate.

5. The bone plate of claim 1, wherein the plate includes first and second outer lateral sidewalls, wherein at least a portion of the first and second outer sidewalls adjacent to a bone screw hole is curved.

6. The bone plate of claim 1, wherein each of the plurality of cams is integrated with the plate.

7. The bone plate of claim 1, wherein the plurality of cams are aligned on the first and second longitudinal axes.

8. The bone plate of claim 1, wherein each of the plurality of cams is configured to engage a bone screw disposed in a bone screw hole adjacent to the cam when the cam is in the locked position.

9. The bone plate of claim 1, wherein the width of the mid-portion extends from the first longitudinal axis to the second longitudinal axis.

10. The bone plate of claim 1, wherein a height of the window is greater than the width of the mid-portion of the plate.

11. An implantable bone plate, comprising:
an elongate plate having first and second parallel longitudinal axes;
a plurality of bone screw holes, the bone screw holes being aligned on the first and second longitudinal axes in laterally adjacent pairs;
a plurality of rotatable cams each being disposed adjacent to a respective one of the plurality of bone screw holes, each cam being rotatable between an unlocked position and a locked position; and
a window formed in the plate and extending longitudinally between the laterally adjacent pairs of bone screw holes, the window having:
a superior portion defined by opposed lateral sidewalls and a superior sidewall, the superior portion being at least partially disposed between first and second cams of the plurality of cams,
an inferior portion defined by opposed lateral sidewalls and an inferior sidewall, and
a mid-portion extending between the superior and inferior portions, the mid-portion having a width extending between opposed lateral sidewalls that is greater than a width extending between the opposed lateral sidewalls of the superior and inferior portions,
wherein the lateral sidewalls of the inferior portion of the window are parallel and the lateral sidewalls of the superior portion of the window are parallel.

12. An implantable bone plate, comprising:
an elongate plate having first and second parallel longitudinal axes;
a plurality of bone screw holes, the bone screw holes being aligned on the first and second longitudinal axes in laterally adjacent pairs;
a plurality of rotatable cams each being disposed adjacent to a respective one of the plurality of bone screw holes, each cam being rotatable between an unlocked position and a locked position; and
a window formed in the plate and extending longitudinally between the laterally adjacent pairs of bone screw holes, the window having:
a superior portion defined by opposed lateral sidewalls and a superior sidewall, the superior portion being at least partially disposed between first and second cams of the plurality of cams, an inferior portion defined by opposed lateral sidewalls and an inferior sidewall, and a mid-portion extending between the superior and inferior portions, the mid-portion having a width extending between opposed lateral sidewalls that is greater than a width extending between the opposed lateral sidewalls of the superior and inferior portions, wherein:

each of the laterally adjacent pairs of bone screw holes has a transverse bone screw plane extending between an edge of each laterally adjacent bone screw hole of the pair;

the superior sidewall of the superior portion of the window extends at least to the transverse bone screw hole plane of a first laterally adjacent pair of bone screw holes; and the inferior sidewall of the inferior portion of the window extends at least to the transverse bone screw hole plane of a second laterally adjacent pair of bone screw holes that is spaced longitudinally from the first adjacent pair of bone screw holes.

13. An implantable bone plate, comprising:
an elongate plate having superior and inferior ends;
a first bone screw hole formed in the plate;
a first locking cam disposed adjacent to the first bone screw hole and being rotatable with respect to the plate between a locked position and an unlocked position;
a second bone screw hole formed in the plate;
a second locking cam disposed adjacent to the second bone screw hole and being rotatable with respect to the plate between a locked position and an unlocked position;
a third bone screw hole formed in the plate;
a third locking cam disposed adjacent to the third bone screw hole and being rotatable with respect to the plate between a locked position and an unlocked position;
a fourth bone screw hole formed in the plate;
a fourth locking cam disposed adjacent to the fourth bone screw hole and being rotatable with respect to the plate between a locked position and an unlocked position; and
a window formed in the plate;
wherein the first and second bone screw holes are aligned on a first transverse axis of the plate;
wherein the first and second locking cams are aligned on a second transverse axis of the plate that is inferior to the first transverse axis;
wherein the third and fourth locking cams are aligned on a third transverse axis of the plate that is inferior to the second transverse axis;
wherein the third and fourth bone screw holes are aligned on a fourth transverse axis of the plate that is inferior to the third transverse axis;
wherein the first bone screw hole and the third bone screw hole are aligned on a first longitudinal axis of the plate;
wherein the second bone screw hole and the fourth bone screw hole are aligned on a second longitudinal axis of the plate;
wherein the window includes:
a superior portion that extends superior to the second transverse axis;
an inferior portion that extends inferior to the third transverse axis; and
a middle portion extending between the superior and inferior portions and having a transverse dimension that is greater than a transverse dimension of the superior portion and a transverse dimension of the inferior portion.

14. The bone plate of claim 13, wherein the inferior portion of the window includes opposed lateral sidewalls that are parallel to one another and wherein the superior portion of the window includes opposed lateral sidewalls that are parallel to one another.

15. The bone plate of claim 13, further comprising a first stabilizing strut extending between the first and second bone screw holes and a second stabilizing strut extending between the third and fourth bone screw holes.

16. The bone plate of claim 13, wherein:
the superior sidewall of the superior portion of the window extends at least to a transverse bone screw hole plane extending from an edge of the first bone screw hole to an edge of the second bone screw hole; and
the inferior sidewall of the inferior portion of the window extends at least to a transverse bone screw hole plane extending from an edge of the third bone screw hole to an edge of the fourth bone screw hole.

17. The bone plate of claim 13, wherein the superior and inferior portions of the window extend longitudinally and the middle portion of the window extends transversely.

18. The bone plate of claim 13, further comprising recessed areas adjacent to struts at the superior and inferior ends of the plate, the recessed areas being formed in the outer periphery of the plate.

19. The bone plate of claim 13, wherein the plate includes first and second outer lateral sidewalls, wherein at least a portion of the first and second outer sidewalls adjacent to a bone screw hole is curved.

20. The bone plate of claim 13, wherein each of the first, second, third, and fourth locking cams is integrated with the plate.

21. The bone plate of claim 13, wherein the first and third locking cams are aligned on the first longitudinal axis and the second and fourth locking cams are aligned on the second longitudinal axis.

22. The bone plate of claim 13, wherein the first, second, third, and fourth locking cams are configured to engage respective bone screws disposed in the first, second, third, and fourth bone screw holes, respectively, when said first, second, third, and fourth locking cams are in the locked position.

* * * * *